(12) United States Patent
Kanda

(10) Patent No.: US 7,105,188 B2
(45) Date of Patent: Sep. 12, 2006

(54) THERAPEUTIC AGENT OF SKIN DISEASES

(76) Inventor: Mitsuyo Kanda, 3162-1, Aza-Gounaka, Konobunakashima, Bisai-shi, Aichi-ken (JP)

( * ) Notice: Subject to any disclaimer, the term of this patent is extended or adjusted under 35 U.S.C. 154(b) by 153 days.

(21) Appl. No.: 10/916,229

(22) Filed: Aug. 11, 2004

(65) Prior Publication Data

US 2005/0163878 A1    Jul. 28, 2005

(30) Foreign Application Priority Data

Jan. 27, 2004    (JP)    ............... 2004-018118

(51) Int. Cl.
*A01N 65/00*    (2006.01)
(52) U.S. Cl. ............... 424/770; 424/774; 514/858
(58) Field of Classification Search ............... 424/770, 424/774; 514/858
See application file for complete search history.

(56) References Cited

U.S. PATENT DOCUMENTS

2004/0062825 A1*    4/2004    Fukuda

FOREIGN PATENT DOCUMENTS

| JP | 61289865 A | * | 12/1986 |
| JP | 2733007 | | 3/1998 |
| KR | 2000028403 A | * | 5/2000 |
| KR | 2001008095 A | * | 2/2001 |
| WO | EP001297837 A1 | * | 2/2003 |

* cited by examiner

*Primary Examiner*—Michele Flood
(74) *Attorney, Agent, or Firm*—Armstrong, Kratz, Quintos, Hanson & Brooks, LLP

(57) ABSTRACT

Therapeutic agents for skin diseases such as atopic dermatitis and athlete's foot can be obtained from naturally occurring raw materials without requiring the use of steroids and their severe adverse effects. The therapeutic agents contain a fermentation solution as the active component. The fermentation solution is obtained by fermenting raw materials including sugar components, water, and pine leaf or pine leaf clusters. The pine leaf cluster may be a fresh pine leaf cluster, from which the short shoot is preliminarily removed and then the fresh pine leaves are cut into a given length.

13 Claims, 3 Drawing Sheets

THERAPEUTIC AGENT OF SKIN DISEASES

This application claims priority to Japanese patent application serial number 2004-018118, the contents of which are incorporated herein by reference.

BACKGROUND OF THE INVENTION

1. Field of the Invention

The present invention relates to a therapeutic agent for skin diseases, which contains as an active component a fermentation solution of pine leaf.

2. Description of the Related Art

A therapeutic agent for asthma has been known in the related art. The therapeutic agent contains a fermentation solution as the active component. The fermentation solution is prepared by fermenting a sugar component, water, and pine leaf, as the raw materials (the publication of Japanese patent No. 2733007).

Additionally, other therapeutic agents for skin diseases such as atopic dermatitis and athlete's foot have been well known traditionally.

For the therapeutic treatment of atopic dermatitis, therapeutic agents containing steroids are often used. It is known that although steroids strongly act upon various skin diseases, the adverse effects thereof are also strong in proportion to the magnitude of the therapeutic effect. Adverse symptom effects have been known, including for example; rough skin (similar to that of an elephant) via skin shrinkage and a reddish face (blushing) via the dilatation of blood capillaries.

SUMMARY OF THE INVENTION

Accordingly, it is an objective of the invention to provide a therapeutic agent for skin diseases using raw materials obtained from natural origins, with no use of steroids and their associated serious adverse side effects.

The therapeutic agent of the invention is a therapeutic agent containing a fermentation solution as the active component. The fermentation solution is obtained by fermenting raw materials including sugar components, water, and fresh pine leaves (i.e., pine needles)or fresh pine leaf clusters. The therapeutic agent exerts a distinct therapeutic effect on skin diseases including but not limited to atopic dermatitis and athlete's foot.

Additionally, the fermentation solution as the active component of the therapeutic agent of the invention may be prepared by placing raw materials including sugar components, hot water at 80° C. or more, and fresh pine leaves, into one container, and then leaving the container to stand alone for fermentation. By using hot water initially at 80° C. or more as one of the raw materials, the active ingredients in the fresh pine leaves can be extracted instantly so as to prepare a therapeutic agent with a high therapeutic efficacy.

Regarding the pine leaves for use as a raw material of the therapeutic agent of the invention, preferably, fresh pine leaf clusters are used. Fresh pine leaf clusters typically include a short shoot locating at the base or connecting point of two or more individual pine leaves. From the fresh pine leaf cluster, preferably the short shoot is preliminarily removed and then the individual leaves (needles) are cut into a given length. Additionally, the therapeutic agent is preferably sprayable on lesions, as the therapeutic agent may be placed within a sprayer.

In accordance with the invention, a therapeutic agent for skin diseases may be obtained, using raw materials with natural origins, and with no use of steroids and their associated severe adverse effects or the like.

DETAILED DESCRIPTION OF THE INVENTION

Figure 1:
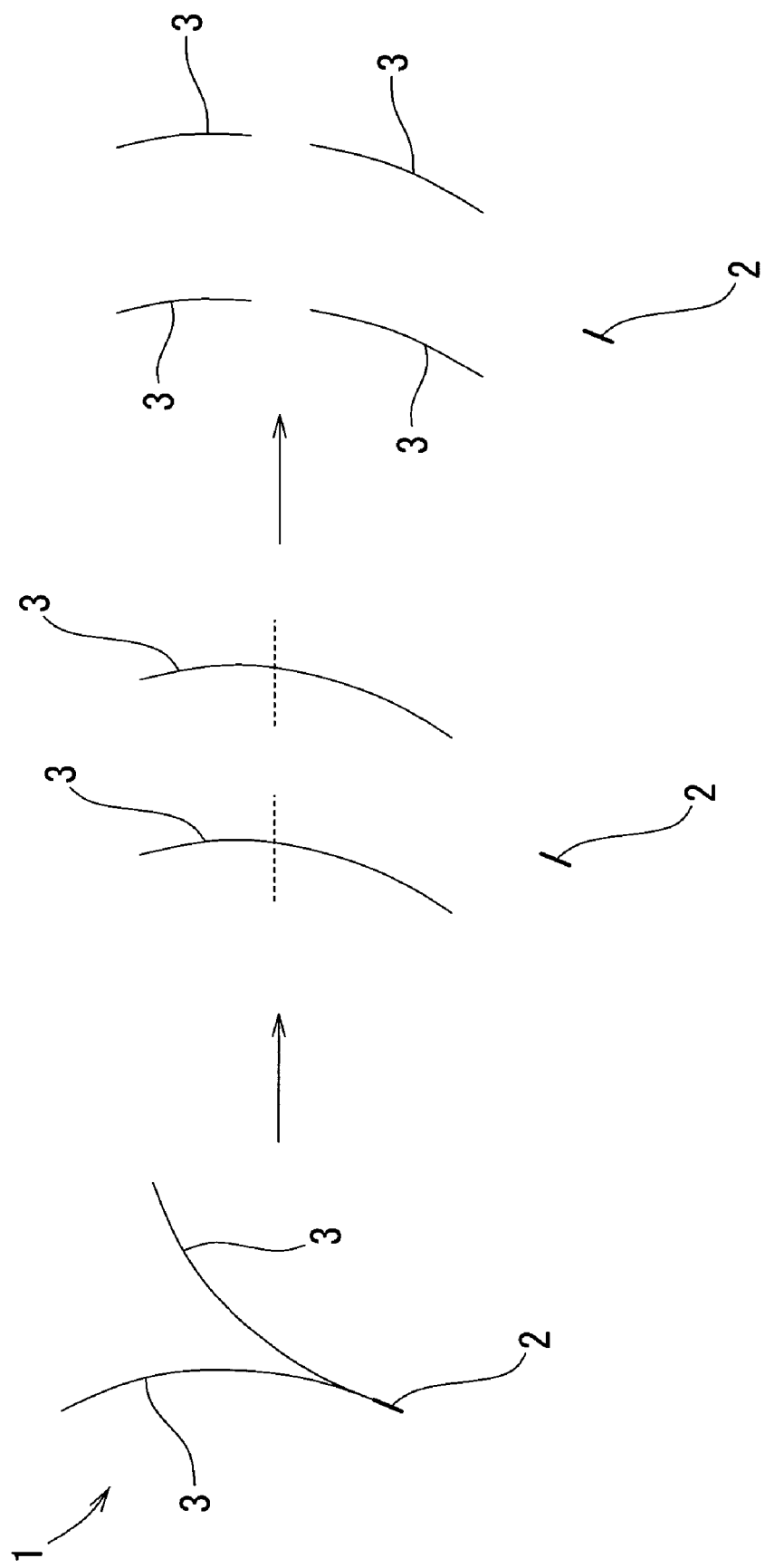
FIG. 1 is an explanatory view describing the procedures for processing a pine leaf cluster.

Each of the additional features and teachings disclosed above and below may be utilized separately or in conjunction with other features and teachings to provide improved therapeutic agent and methods of using such improved therapeutic agent. Representative examples of the present invention, which examples utilize many of these additional features and teachings both separately and in conjunction with one another, will now be described in detail with reference to the attached drawings. This detailed description is merely intended to teach a person of skill in the art further details for practicing preferred aspects of the present teachings and is not intended to limit the scope of the invention. Only the claims define the scope of the claimed invention. Therefore, combinations of features and steps disclosed in the following detailed description may not be necessary to practice the invention in the broadest sense, and are instead taught merely to particularly describe representative examples of the invention. Moreover, various features of the representative examples and the dependent claims may be combined in ways that are not specifically enumerated in order to provide additional useful embodiments of the present teachings.

The therapeutic agent of the invention is a therapeutic agent with distinct therapeutic efficacies on skin diseases such as atopic dermatitis and athlete's foot. The therapeutic agent of the invention contains a fermentation solution as the active component. The fermentation solution is obtained by fermenting raw materials including sugar components, water, and fresh pine leaves or fresh pine leaf clusters.

As the sugar components, any fermentable sugar component may be used, for example crystalline sugar, purified sugar, honeybee, and brown sugar. Any amount of the sugar components may be satisfactorily used with no specific limitation, as long as the fermentation can proceed when using that amount. Regarding the sugar components, preferably, crystalline sugar is used. Because crystalline sugar slowly dissolves in an oral cavity, the sugar component is likely to infiltrate into the tissue of the pine leaf.

Any water suitable for use in therapeutic agents is used, for example distilled water. The temperature of the water is not limited to any particular limitation. Preferably however, hot water at 80° C. or more is used. Specifically, the sugar components, hot water at 80° C. or more, and fresh pine leaves, are placed as the raw materials in one container. The container is then left to stand alone for fermentation, in order to obtain a fermentation solution. A therapeutic agent with high efficacies on skin diseases can be obtained by using the resulting fermentation solution. The reason for the higher therapeutic efficacies lies in the use of hot water at 80° C. or more for instant extraction of the active ingredients in pine leaf.

Regarding the pine leaf for use as a raw material, fresh pine leaf is preferable. Fresh pine leaf means pine leaf used shortly after collection from a pine tree. Fresh pine leaf for use as a raw material is preferably fresh green leaf. Withered, brown, or yellow pine leaves are preferably avoided. In the case where the pine leaves collected from a pine tree are not to be immediately used, the fresh pine leaves are preferably sealed in a highly sealable container, such as a polyethylene bag, and are then stored in a refrigerator or other cool place. Regarding which pine leaf to use, various pine leaves can be used such as those of *Pinus densiflora* (red pine) and *Pinus thunbergii* (black pine). The use of the leaves of *Pinus densiflora* from a cold region (for example, the Nagano prefecture or Gifu prefecture of Japan) produces a therapeutic agent with a higher therapeutic efficacy.

The part referred to as the "leaf" of a pine tree is developed from the ramenta of short shoots. Plural pine leaves are connected at their bases through a part called a short shoot (or leaf shoot) forming a pine leaf cluster. In accordance with the invention, a pine leaf cluster using plural such leaves in connection may be used. However, a therapeutic agent with higher efficacies can be obtained when the short shoot is removed to separate the leaves into each individual pine leaf, and then each individual pine leaf is cut into a given length or lengths prior to use. This may aid the ready extraction of the pine leaf extract in water.

Fermentation, spontaneously induced, may be utilized for fermenting the raw materials by mixing the sugar components, water, and fresh pine leaves together, and leaving the resulting mixture to stand alone. Additionally, fermentation may be induced by other known artificial methods. As for the fermentation method, appropriate methods may be used. In the case of using spontaneously occurring fermentation, fermentation is completed in about 20 days during summer or in about 2 months during winter, depending upon the location where the container is arranged holding the raw materials therein. In order to confirm the completion of fermentation, the contents of the container should be inspected using visual observation to verify that the foaming within the container has stopped.

Further, for the therapeutic agent of the invention, a fermentation solution that has not yet been completely fermented may also be used. There is no specific limitation to the degree of the progress of fermentation, but a fermentation solution at an advanced stage of fermentation or at the completion stage of fermentation is preferably used because the effect of the therapeutic agent is likely to be larger.

The fermentation solution obtained by fermenting raw materials such as sugar components, water, and fresh pine leaves, may be applied directly to lesions or may be coated on lesions after dilution with water. For a higher exertion of the effect as a therapeutic agent, the fermentation solution is preferably coated on lesions as an undiluted stock solution. For therapeutic treatment of atopic dermatitis, generally, the fermentation solution is coated on lesions on a continuous daily basis approximately twice to three times daily, to exert a therapeutic effect. In case of the therapeutic treatment of athlete's foot, generally, the fermentation solution is coated on lesions on a continuous daily basis approximately four to five times daily, to exert a therapeutic effect. Depending on the severity of the symptoms, the therapeutic effect typically emerges in about one week from the start of treatment (i.e., coating).

The fermentation solution obtained by fermenting raw materials including sugar components, water, and fresh pine leaves or fresh pine leaf clusters, may be immersed or saturated into gauze and the like for coating or covering lesions. Otherwise, the fermentation solution may be coated directly on lesions by pouring the fermentation solution into the palm of a hand and subsequently applying the fermentation solution with the hands. More preferably, the fermentation solution is placed in a sprayer, from which the fermentation solution may be directly sprayed upon lesions. By spraying the fermentation solution on lesions, the fermentation solution can be uniformly applied (coated) on lesions. In the case of using a sprayer as described above, the coating of the fermentation solution on lesions is effectively easy to perform.

It is also confirmed that the therapeutic agent of the invention shows a therapeutic effect on skin diseases other than atopic dermatitis and athlete's foot. It is verified that the therapeutic agent of the invention may at least exert a therapeutic effect on, for example, bruises, eruptions, and insect bites.

EXAMPLES

Specific examples of the invention are now described with reference to FIGS. 1, 2, and 3.

FIG. 1 is an explanatory view describing the procedures for processing a pine leaf cluster 1. In the present Example, a pine leaf cluster 1 of *Pinus densiflora* from the Nagano prefecture or Gifu prefecture in Japan is used. After a fresh green pine leaf cluster 1 is rinsed, the short shoot 2, existing at the part where the bases of two pine leaves are connected together, is removed. In such a manner, two pine leaves 3 are separated. The separated pine leaves 3 are cut at approximately a half-length for use as a raw material for the fermentation solution.

Figure 2:
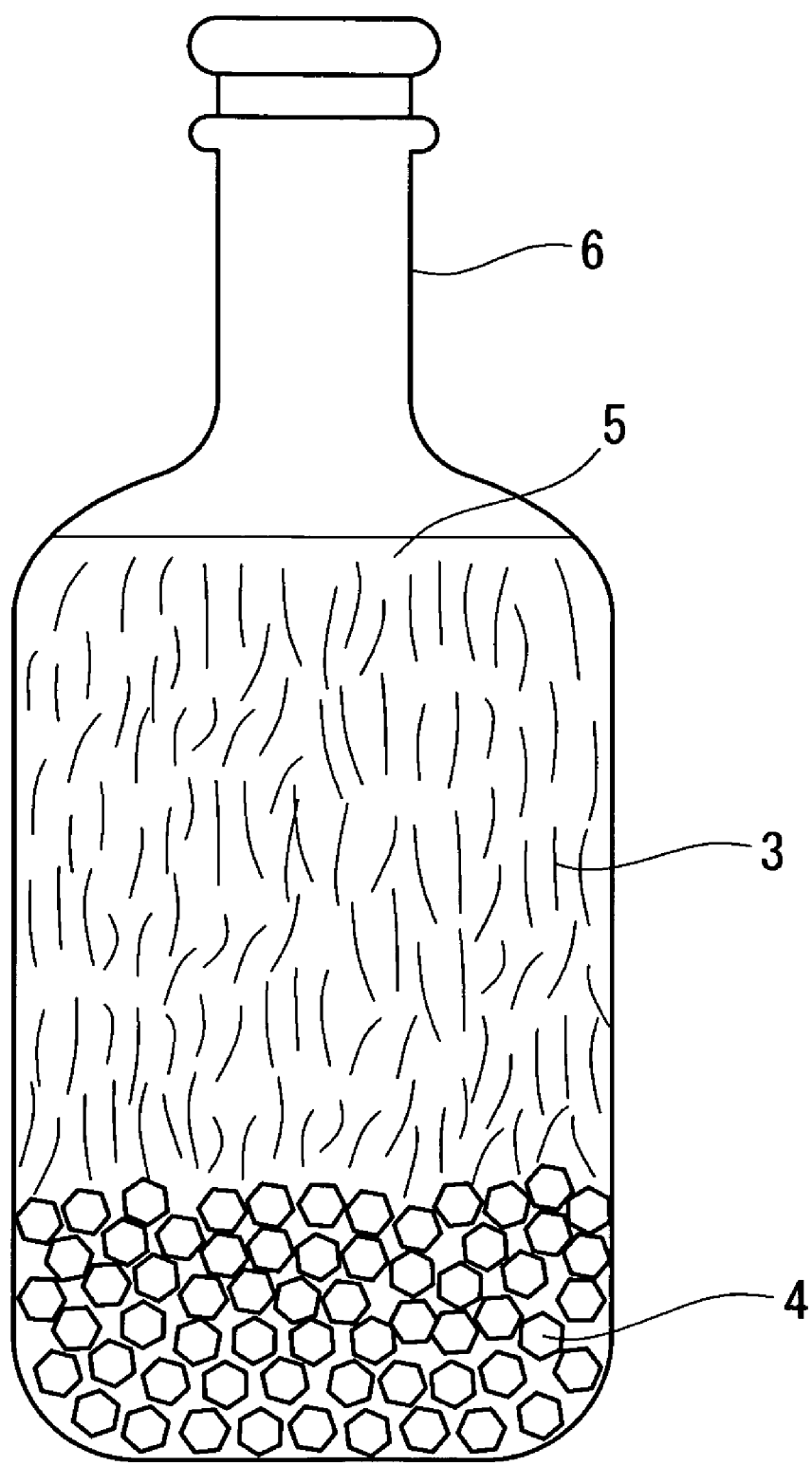
FIG. 2 shows a glass container placing therein crystalline sugar, distilled water, and fresh pine leaves.

FIG. 2 shows glass container 6 placing therein crystalline sugar 4, distilled water 5, and cut fresh pine leaves 3.

So as to ferment the fresh pine leaf 3 blades (needles) in order to obtain a fermentation solution, about 300 g of crystalline sugar 4 is placed in the bottom of a previously rinsed and sterilized glass container 6. On top of the crystalline sugar 4 is placed about 300 g of the pine leaves 3, each cut into approximately half of their original length during the previous step. Then, about 1.3 liters of distilled water 5 is heated to a temperature of 80° C. or more, and poured into the container 6. When the container 6 is left to stand, fermentation of the raw materials, including the pine leaves 3 and the like, progresses over time, inducing foaming in the container 6. During summer, the foaming would typically terminate in approximately 20 days.

After the completion of fermentation, only the fermentation solution in the container 6 is gently transferred to a different container. The fermentation solution at an almost complete stage of fermentation is transferred in order to obtain a highly efficacious therapeutic agent. The fermentation solution may be satisfactorily coated on lesions in a state dispersed into gauze or the like. After dilution with water, the resulting fermentation solution may also be coated on lesions.

Figure 3:
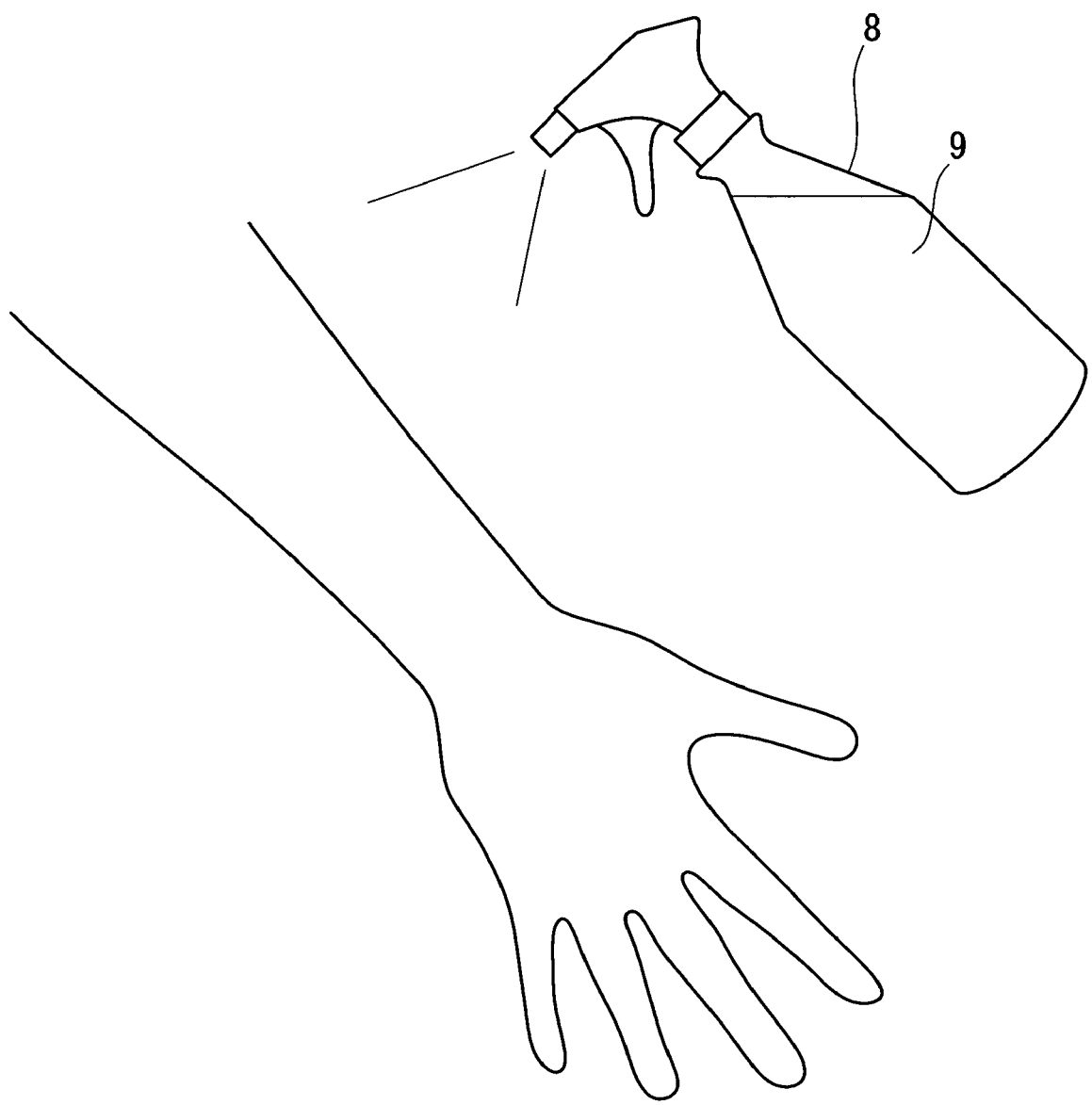
FIG. 3 shows a state where a fermentation solution of pine leaf is placed in a sprayer, from which the fermentation solution is directly applied to lesions.

FIG. 3 shows a state of the fermentation solution 9 of pine leaves as placed within sprayer 8, from which the fermentation solution 9 is directly applied to (or sprayed upon) the lesions.

In order to consistently coat the fermentation solution 9 of pine leaves upon the lesions, the resulting fermentation solution is conveniently placed within the sprayer 8, as shown in FIG. 3. By placing the fermentation solution 9 in the sprayer 8, the fermentation solution 9 may be sprayed uniformly on lesions.

The fermentation solution obtained by the method described above was coated on the upper half of the body of a patient with atopic dermatitis (male, age 7 years old). About 30 cc/application of the fermentation solution was applied in a continuous coat at a frequency of two to three times per day. When approximately 720 cc of the fermentation solution was consumed, the symptoms of the atopic dermatitis were improved to a condition close to an almost completely cured state. Additionally, the child patient had been unwilling to use a steroid-containing therapeutic agent. However, the fermentation solution of pine leaves could be coated in a very easy manner. This may be due in part to the reason that the fermentation solution of pine leaves is a white, tasteful liquid, and is a therapeutic agent with no significant adverse effects on bodies, even when it is ingested. Additionally, the fermentation solution of pine leaf is prepared from naturally occurring raw materials and is therefore a therapeutic agent with no significant occurrence of adverse effects such as allergic reactions.

In another case, the fermentation solution of pine leaves was coated on the lesions of an adult male patient with neck skin resembling elephant skin due to the continuous use of a steroid therapeutic agent. Approximately 10 cc/application of the fermentation solution was applied in a continuous coat at a frequency of two to three times per day. When about 300 cc of the fermentation solution was consumed, the skin condition was improved to a state close to an almost completely cured state.

In a still additional case, the fermentation solution of pine leaves was coated upon the lesions of the athlete's foot of an adult male patient. About 10 cc/application of the fermentation solution was applied in a continuous coat upon the athlete's foot lesions on the toes of the patient at a frequency of four to five times per day. The damp and oozy symptoms of athlete's foot were improved in approximately a week to a state close to an almost completely cured state.

In a further case, the fermentation solution of pine leaves was additionally coated upon the lesions of eruptions upon the whole area of the feet of an adult male patient. About 30 cc/application of the fermentation solution was applied in a continuous coat upon the lesions at a frequency of two to three times per day. The eruption symptoms were improved in about two weeks to a condition close to an almost completely cured state. For this particular patient, the eruptions had been so itchy that the bleeding from the lesions may never have been stopped. Coating of the fermentation solution of pine leaves essentially completely eliminated the itchy and bleeding symptoms.

What is claimed is:

1. A therapeutic agent for skin diseases,
   wherein the therapeutic agent contains a fermentation solution as the active component, and
   wherein the fermentation solution is obtained by fermenting raw materials in a container,
   wherein the raw materials comprise,
      a sugar component, and
      water at 80° C. or more, and
      a pine leaf cluster, and
   wherein the fermenting comprises leaving the container to stand for a period of time.

2. The therapeutic agent for skin diseases according to claim 1, wherein the pine leaf cluster comprises fresh pine leaves connected through a short shoot, said short shot being removed therefrom, and
   wherein the pine leaves are cut into a given length.

3. The therapeutic agent of skin diseases according to claim 2, wherein the therapeutic agent is placed within a sprayer, and
   wherein the therapeutic agent is applied by spraying the agent upon a treatment area.

4. The therapeutic agent for skin diseases according to claim 1, wherein the therapeutic agent is placed within a sprayer, and
   wherein the therapeutic agent is applied by spraying the agent upon a treatment area.

5. A therapeutic agent for atopic dermatitis,
   wherein the therapeutic agent contains a fermentation solution as the active component, and
   wherein the fermentation solution is obtained by fermenting raw materials in a container,
   wherein the raw materials include
      a sugar component, and
      water at 80 °C. or more, and
      a pine leaf cluster, and
   wherein the fermenting comprises leaving the container to stand for a period of time.

6. The therapeutic agent for atopic dermatitis according to claim 5, wherein the pine leaf cluster comprises fresh pine leaves connected through a short shoot, said short shoot being removed therefrom, and
   wherein the pine leaves are cut into a given length.

7. The therapeutic agent for atopic dermatitis according to claim 6, wherein the therapeutic agent is placed within a sprayer, and
   wherein the therapeutic agent is applied by spraying the agent upon lesions.

8. The therapeutic agent for atopic dermatitis according to claim 5, wherein the therapeutic agent is placed within a sprayer, and
   wherein the therapeutic agent is applied by spraying the agent upon lesions.

9. A therapeutic agent of athlete's foot, wherein the therapeutic agent contains a fermentation solution as the active component, and
   wherein the fermentation solution is obtained by fermenting raw materials in a container,
   wherein the raw materials include
      a sugar component, and
      water at 80° C. or more and
      a pine leaf cluster, and
   wherein the fermenting comprises leaving the container to stand for a period of time.

10. The therapeutic agent for athlete's foot according to claim 9, wherein the pine leaf cluster comprises, two or more pine leafs
    the pine leaf cluster comprises fresh pine leaves connected through a short shoot, said short shoot being removed therefrom, and
    wherein the pine leaves are cut into a given length.

11. The therapeutic agent for athlete's foot according to claim 10, wherein the therapeutic agent is placed within a sprayer, and
    wherein the therapeutic agent is applied by spraying the agent upon lesions.

12. The therapeutic agent for athlete's foot according to claim 9, wherein the therapeutic agent is placed within a sprayer, and
    wherein the therapeutic agent is applied by spraying the agent upon lesions.

13. A therapeutic agent for skin diseases,
    wherein the therapeutic agent contains a fermentation solution as the active component,
    wherein the fermentation solution is obtained by fermenting raw materials in a container,
    wherein the raw materials comprise,
       a sugar component, and
       water at 80° C. or more, and
       at least one pine leaf, and
    wherein the fermenting comprises leaving the container to stand for a period of time.

* * * * *